United States Patent
Ueda et al.

(10) Patent No.: US 10,144,814 B2
(45) Date of Patent: Dec. 4, 2018

(54) ULTRAVIOLET ABSORBER AND SYNTHETIC RESIN COMPOSITION

(71) Applicant: ADEKA CORPORATION, Tokyo (JP)

(72) Inventors: Naoto Ueda, Saitama (JP); Kazukiyo Nomura, Saitama (JP)

(73) Assignee: ADEKA CORPORATION, Tokyo (JP)

( * ) Notice: Subject to any disclaimer, the term of this patent is extended or adjusted under 35 U.S.C. 154(b) by 0 days.

(21) Appl. No.: 15/503,177

(22) PCT Filed: Nov. 11, 2015

(86) PCT No.: PCT/JP2015/081711
§ 371 (c)(1),
(2) Date: Feb. 10, 2017

(87) PCT Pub. No.: WO2016/080259
PCT Pub. Date: May 26, 2016

(65) Prior Publication Data
US 2017/0233551 A1    Aug. 17, 2017

(30) Foreign Application Priority Data

Nov. 17, 2014 (JP) ................................. 2014-233084
Oct. 26, 2015 (JP) ................................. 2015-209682

(51) Int. Cl.
| | |
|---|---|
| *C08K 5/3492* | (2006.01) |
| *C07D 251/24* | (2006.01) |
| *C09K 3/00* | (2006.01) |
| *C08L 101/00* | (2006.01) |
| *C08K 5/053* | (2006.01) |
| *C08K 5/132* | (2006.01) |
| *C08K 5/134* | (2006.01) |

(52) U.S. Cl.
CPC .......... *C08K 5/3492* (2013.01); *C07D 251/24* (2013.01); *C08L 101/00* (2013.01); *C09K 3/00* (2013.01); *C08K 5/053* (2013.01); *C08K 5/132* (2013.01); *C08K 5/134* (2013.01)

(58) Field of Classification Search
None
See application file for complete search history.

(56) References Cited

U.S. PATENT DOCUMENTS

| | | |
|---|---|---|
| 7,125,920 B2 | 10/2006 | Negishi et al. |
| 7,449,577 B2 | 11/2008 | Kimura et al. |
| 7,553,892 B2 | 6/2009 | Negishi et al. |
| 7,842,744 B2 | 11/2010 | Negishi et al. |
| 8,287,778 B2 | 10/2012 | Fukushima et al. |
| 8,293,145 B2 | 10/2012 | Negishi et al. |
| 8,444,884 B2 | 5/2013 | Futterer et al. |
| 8,940,818 B2 | 1/2015 | Futterer et al. |
| 2012/0322923 A1 | 12/2012 | Wermter et al. |
| 2014/0155528 A1 | 6/2014 | Onoue et al. |
| 2014/0288217 A1 | 9/2014 | Hatanaka et al. |

FOREIGN PATENT DOCUMENTS

| | | | |
|---|---|---|---|
| CN | 1694919 | 11/2005 | |
| CN | 1845913 | 10/2006 | |
| CN | 1957270 | 5/2007 | |
| CN | 101772537 | 7/2010 | |
| CN | 102047154 | 5/2011 | |
| CN | 102282206 | 12/2011 | |
| CN | 102741335 | 10/2012 | |
| CN | 103635534 | 3/2014 | |
| CN | 103827197 | 5/2014 | |
| EP | 0165608 A2 * | 12/1985 | ........... C07D 251/22 |
| JP | 61-24577 | 2/1986 | |
| JP | 11-71326 | 3/1999 | |
| JP | 2001-302926 | 10/2001 | |

OTHER PUBLICATIONS

Conn, G. and Eisler, S., "Synthesis and Intramolecular Hydrogen Bonding Networks of 2,4,6-Tri(o-hydroxyaryl)-1,3,5-Triazines". Organic Letters 2011, 13(19), 5080-5083. (Year: 2011).*
International Search Report, PCT/JP2015/081711, dated Feb. 9, 2016.

* cited by examiner

*Primary Examiner* — Richard A Huhn
(74) *Attorney, Agent, or Firm* — Young & Thompson

(57) ABSTRACT

Provided is an ultraviolet absorbing agent that efficiently absorbs ultraviolet rays in a wide wavelength region, and in particular, has a strong absorbability in the UV-A region. Also, a synthetic resin composition having excellent weatherability is provided. Provided is an ultraviolet absorbing agent including a triazine-based compound represented by Formula (1) below. Also, a synthetic resin composition containing the ultraviolet absorbing agent is provided. $R^2$, $R^3$, and $R^4$ in the triazine-based compound represented by Formula (1) below are each preferably a hydrogen atom or a methyl group, and particularly preferably a hydrogen atom.

7 Claims, No Drawings

ULTRAVIOLET ABSORBER AND SYNTHETIC RESIN COMPOSITION

TECHNICAL FIELD

The present invention relates to an ultraviolet absorbing agent including a triazine-based compound having a specific structure, and a synthetic resin composition blended with the ultraviolet absorbing agent. Specifically, the present invention relates to an ultraviolet absorbing agent that absorbs ultraviolet rays in a wide range and has excellent ultraviolet absorbability, and a synthetic resin composition that is blended with the ultraviolet absorbing agent and has excellent weatherability.

BACKGROUND ART

Sunlight includes ultraviolet rays, and in order to prevent deterioration and damage caused by the ultraviolet rays, ultraviolet absorbing agents are widely used in synthetic resins, paints, fibers, macromolecular film, cosmetics, and the like.

The ultraviolet rays in the sunlight have wavelengths of UV-A rays (having a wavelength of 315 to 400 nm), UV-B rays (having a wavelength of 280 to 315 nm), and UV-C rays (200 to 280 inn). Among these, ultraviolet rays in the UV-C region do not reach the ground. Therefore, the ultraviolet absorbing agent that can efficiently absorb ultraviolet rays in the UV-A region and the UV-B region, of the above-described wavelengths has been in demand.

For example, a triazine-based ultraviolet absorbing agent has been proposed to meet the above-described demand (Patent Literature 1 and 2). However, the ultraviolet absorbability of these conventional ultraviolet absorbing agents is not satisfying, and in particular, they are problematic in the absorbability for ultraviolet rays in the UV-A region.

CITATION LIST

Patent Literature

Patent Literature 1: JP H11-71356A
Patent Literature 2: JP 2001-302926A

SUMMARY OF INVENTION

Technical Problem

Thus, an object of the present invention is to provide an ultraviolet absorbing agent that efficiently absorbs ultraviolet rays in a wide wavelength region, and in particular, has a strong absorbability even in the UV-A region. Also, an object of the present invention is to provide a synthetic resin composition that is blended with the ultraviolet absorbing agent and has excellent weatherability.

As a result of intensive studies to resolve the above-described issues, the inventors of the present invention found a triazine-based ultraviolet absorbing agent having a specific structure, and accomplished the present invention.

That is, the present invention provides an ultraviolet absorbing agent including a triazine-based compound represented by Formula (1).

[Chem. 1]

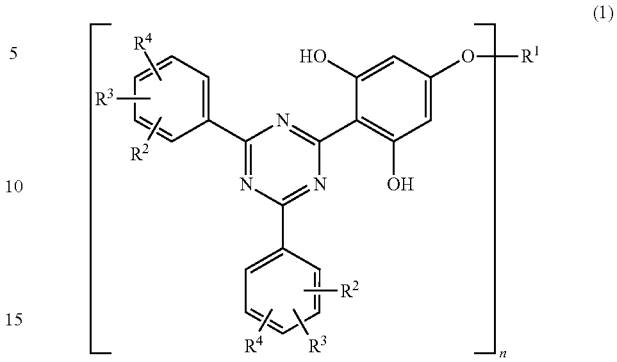

(1)

in the formula, n indicates 1 or 2, when n is 1, $R^1$ represents a hydrogen atom, an alkyl group having 1 to 20 carbon atoms, a cycloalkyl group having 3 to 8 carbon atoms, an alkenyl group having 3 to 8 carbon atoms, an aryl group having 6 to 18 carbon atoms, an alkylaryl group having 7 to 19 carbon atoms, an arylalkyl group having 7 to 19 carbon atoms, or a glycidyl group, when n is 2, $R^1$ represents an alkylene group having 1 to 20 carbon atoms, a cycloalkylene group having 3 to 8 carbon atoms, an arylene group having 6 to 18 carbon atoms, or a combination thereof, each group represented by $R^1$ is optionally substituted with an alkyl group having 1 to 8 carbon atoms, an alkoxy group having 1 to 8 carbon atoms, an aryl group having 6 to 12 carbon atoms, an alkylaryl group having 7 to 13 carbon atoms, an arylalkyl group having 7 to 13 carbon atoms, a hydroxy group, a halogen atom, or a glycidyl group, and is optionally interrupted with an oxygen atom, a sulfur atom, a carbonyl group, an ester group, an amide group, or an imido group, or these substitution and interruption are optionally combined, and $R^2$, $R^3$, and $R^4$ may be identical to or different from each other, and each represent a hydrogen atom, a halogen atom, a hydroxy group, an alkyl group having 1 to 4 carbon atoms, or an alkoxy group having 1 to 4 carbon atoms.

In the present invention, the triazine-based compound represented by Formula (1) is preferably a triazine-based compound represented by Formula (2).

[Chem. 2]

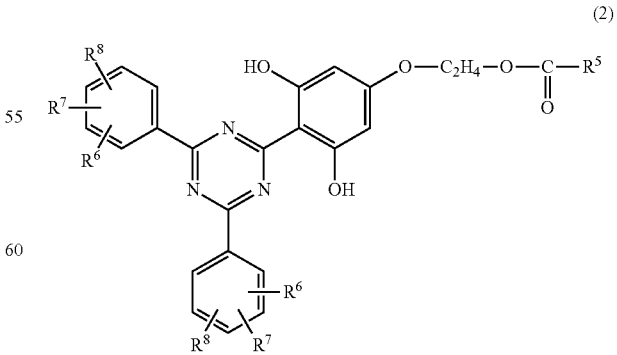

(2)

In the formula, $R^5$ represents a linear or branched alkyl group having 1 to 12 carbon atoms, and $R^6$, $R^7$, and $R^8$ may be identical to or different from each other, and each represent a hydrogen atom or a linear or branched alkyl group having 1 to 4 carbon atoms.

Further, the present invention provides a synthetic resin composition including a synthetic resin and the above-mentioned ultraviolet absorbing agent.

DESCRIPTION OF EMBODIMENTS

Hereinafter, the present invention will be described in detail.

A triazine-based compound that is an ultraviolet absorbing agent of the present invention has a structure represented by Formula (1) below.

[Chem. 3]

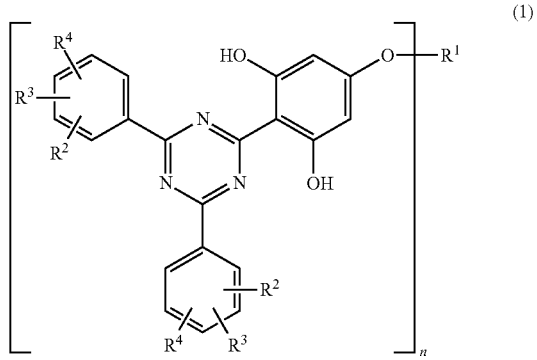

(1)

In Formula (1), n indicates 1 or 2. When n is 1, $R^1$ represents a hydrogen atom, an alkyl group having 1 to 20 carbon atoms, a cycloalkyl group having 3 to 8 carbon atoms, an alkenyl group having 3 to 8 carbon atoms, an aryl group having 6 to 18 carbon atoms, an alkylaryl group having 7 to 19 carbon atoms, an arylalkyl group having 7 to 19 carbon atoms, or a glycidyl group. When n is 2, $R^1$ represents an alkylene group having 1 to 20 carbon atoms, a cycloalkylene group having 3 to 8 carbon atoms, an arylene group having 6 to 18 carbon atoms, or a combination thereof. Each group represented by $R^1$ is optionally substituted with an alkyl group having 1 to 8 carbon atoms, an alkoxy group having 1 to 8 carbon atoms, an aryl group having 6 to 12 carbon atoms, an alkylaryl group having 7 to 13 carbon atoms, an arylalkyl group having 7 to 13 carbon atoms, a hydroxy group, a halogen atom, or a glycidyl group. Also, each group represented by $R^1$ is optionally interrupted by an oxygen atom, a sulfur atom, a carbonyl group, an ester group, an amide group, or an imido group. These substitution and interruption may be combined.

In Formula (1) above, when n is 1, the alkyl group having 1 to 20 carbon atoms represented by $R^1$ may be a liner alkyl group or a branched alkyl group, and examples thereof include a methyl group, an ethyl group, a propyl group, an isopropyl group, a butyl group, an isobutyl group, a sec-butyl group, a tert-butyl group, an amyl group, an isoamyl group, a ten-amyl group, a hexyl group, a heptyl group, a 1-ethylpentyl group, an isoheptyl group, a tert-heptyl group, an octyl group, an isooctyl group, a sec-octyl group, a tert-octyl group, a 2-ethylhexyl group, a nonyl group, an isononyl group, a decyl group, an undecyl group, a dodecyl group, a tridecyl group, a tetradecyl group, a pentadecyl group, a hexadecyl group, a heptadecyl group, an octadecyl group, a nonadecyl group, and an icosyl group.

When n is 1, examples of the cycloalkyl group having 3 to 8 carbon atoms represented by $R^1$ include a cyclopropyl group, a cyclopentyl group, a cyclohexyl group, a cycloheptyl group, and a cyclooctyl group.

When n is 1, examples of the alkenyl group having 3 to 8 carbon atoms represented by $R^1$ include alkenyl groups corresponding to alkyl groups having 3 to 8 carbon atoms of the alkyl groups having 1 to 20 carbon atoms.

When n is 1, examples of the aryl group having 6 to 18 carbon atoms represented by $R^1$ include a phenyl group, a naphthyl group, and a biphenyl group.

When n is 1, examples of the alkylaryl group having 7 to 19 carbon atoms represented by $R^1$ include a methylphenyl group, a dimethylphenyl group, an ethylphenyl group, and an octylphenyl group.

When n is 1, examples of the arylalkyl group having 7 to 19 carbon atoms represented by $R^1$ include a benzyl group, a 2-phenylethyl group, a 1-methyl-1-phenylethyl group, and a 2-phenylpropan-2-yl group.

Also, in Formula (1) above, when n is 2, examples of the alkylene group having 1 to 20 carbon atoms represented by $R^1$ include a methylene group, an ethylene group, a propylene group, a butylene group, a pentylene group, a hexylene group, a heptylene group, an octylene group, a nonylene group, a decylene group, an undecylene group, a dodecylene group, a tridecylene group, a tetradecylene group, a pentadecylene group, a hexadecylene group, a heptadecylene group, an octadecylene group, a nonadecylene group, and an icosylene group.

When n is 2, examples of the cycloalkylene group having 3 to 8 carbon atoms represented by $R^1$ include a cyclopropylene group, a cyclopentylene group, a cyclohexylene group, a cycloheptylene group, and a cyclooctylene group.

When n is 2, examples of the arylene group having 6 to 18 carbon atoms represented by $R^1$ include a phenylene, a tolylene, a xylylene, a naphthylene, and a biphenylene.

Examples of the alkyl group having 1 to 8 carbon atoms with which each group represented by $R^1$ is optionally substituted include alkyl groups having 1 to 8 carbon atoms of the above-described alkyl groups having 1 to 20 carbon atoms.

Examples of the alkoxy group having 1 to 8 carbon atoms with which each group represented by $R^1$ is optionally substituted include alkoxy groups corresponding to alkyl groups having 1 to 8 carbon atoms of the above-described alkyl groups having 1 to 20 carbon atoms.

Examples of the aryl group having 6 to 12 carbon atoms with which each group represented by $R^1$ is optionally substituted include aryl groups having 6 to 12 carbon atoms of the above-described aryl groups having 6 to 18 carbon atoms.

Examples of the alkylaryl group having 7 to 13 carbon atoms with which each group represented by $R^1$ is optionally substituted include alkylaryl groups having 7 to 13 carbon atoms of the above-described alkylaryl groups having 7 to 19 carbon atoms. Examples of the arylalkyl group having 7 to 13 carbon atoms with which each group represented by $R^1$ is optionally substituted include arylalkyl groups having 7 to 13 carbon atoms of the above-described arylalkyl groups having 7 to 19 carbon atoms.

Examples of a halogen atom with which each group represented by $R^1$ is optionally substituted and halogen atoms represented by $R^2$, $R^3$, and $R^4$ include fluorine, chlorine, bromine, and iodine.

Also, in Formula (1), the alkyl group having 1 to 4 carbon atoms represented by $R^2$, $R^3$, and $R^4$ may be a linear alkyl group or a branched alkyl group, and examples thereof include a methyl group, an ethyl group, a propyl group, an isopropyl group, a butyl group, a sec-butyl group, a tert-butyl group, and an isobutyl group, and examples of the alkoxy group having 1 to 4 carbon atoms include alkoxy groups corresponding to the alkyl groups having 1 to 4 carbon atoms.

$R^2$, $R^3$, and $R^4$ are each preferably a hydrogen atom or a methyl group in view of an ultraviolet absorbability and compatibility with a synthetic resin, and particularly preferably a hydrogen atom.

The triazine-based compound represented by Formula (1) is preferably a triazine-based compound represented by Formula (2) below in view of an ultraviolet absorbability and a compatibility with a synthetic resin.

[Chem. 4]

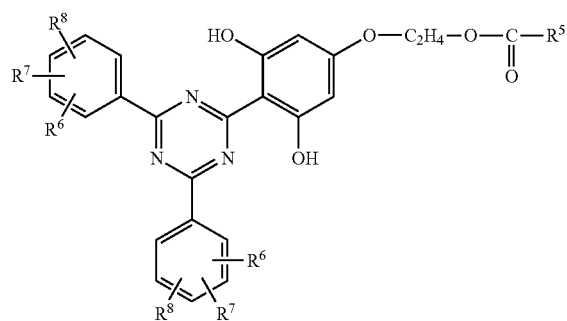

(2)

In Formula (2), $R^5$ represents a linear or branched alkyl group having 1 to 12 carbon atoms. $R^6$, $R^7$, and $R^8$ may be identical to or different from each other, and each represent a hydrogen atom or a linear or branched alkyl group having 1 to 4 carbon atoms.

In Formula (2), examples of the linear or branched alkyl group having 1 to 12 carbon atoms represented by $R^5$ include a methyl group, an ethyl group, a propyl group, an isopropyl group, a butyl group, an isobutyl group, a sec-butyl group, a tert-butyl group, an amyl group, an isoamyl group, a tert-amyl group, a hexyl group, a heptyl group, a 1-ethylpentyl group, an isoheptyl group, a tert-heptyl group, an octyl group, an isooctyl group, a sec-octyl group, a tert-octyl group, a 2-ethylhexyl group, a nonyl group, an isononyl group, a decyl group, an undecyl group, and a dodecyl group, and among these groups, the 1-ethylpentyl group is preferable in view of an ultraviolet absorbability and a compatibility with a synthetic resin.

In Formula (2), examples of the linear or branched alkyl group having 1 to 4 carbon atoms represented by $R^6$, $R^7$, and $R^8$ include a methyl group, an ethyl group, a propyl group, an isopropyl group, a butyl group, a sec-butyl group, a tert-butyl group, and an isobutyl group, and a hydrogen atom or a methyl group is preferable in view of an ultraviolet absorbability and a compatibility with a synthetic resin, and a hydrogen atom is particularly preferable.

The ultraviolet absorbing agent of the present invention has a strong absorbability for ultraviolet rays having wavelengths in both the UV-A region and the UV-B region, and in particular, has a strong absorbability for ultraviolet rays having wavelengths in the UV-A region.

Examples of the triazine-based compound of the present invention represented by Formula (1) above include compounds of Compounds No. 1 to No. 20 below.

[Chem. 5]

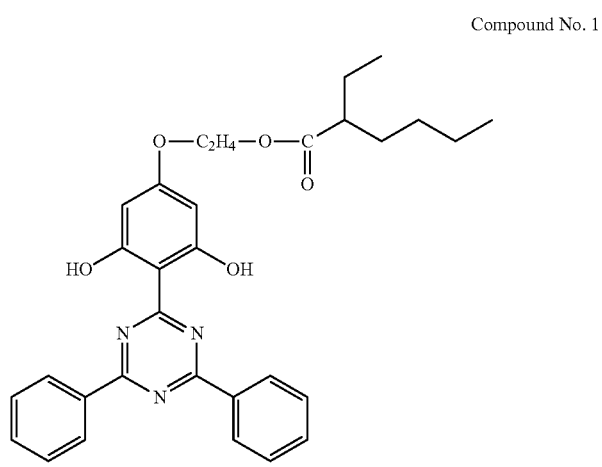

Compound No. 1

[Chem. 6]

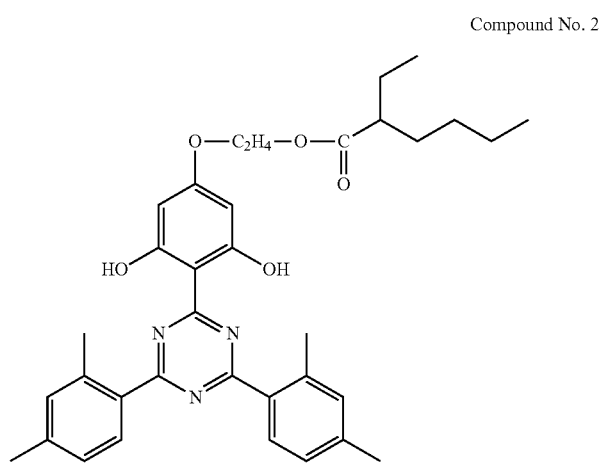

Compound No. 2

-continued
[Chem. 7]
Compound No. 3
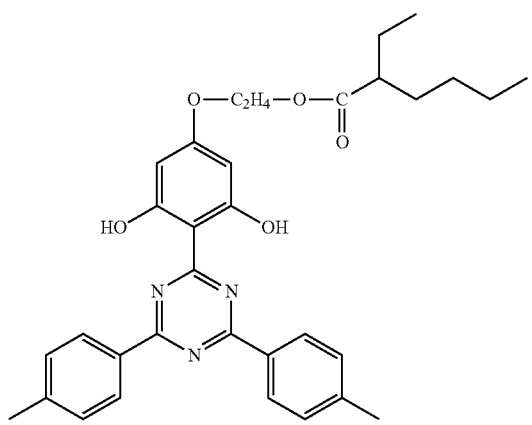
[Chem. 8]
Compound No. 4
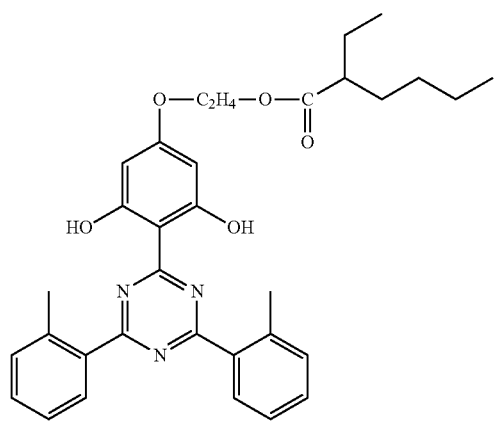
[Chem. 9]
Compound No. 5
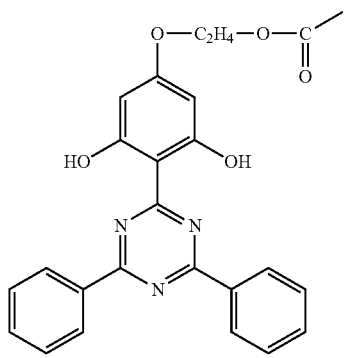
[Chem. 10]
Compound No. 6
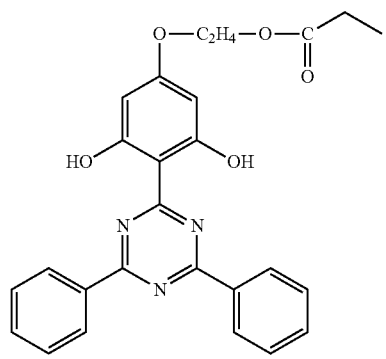
[Chem. 11]
Compound No. 7
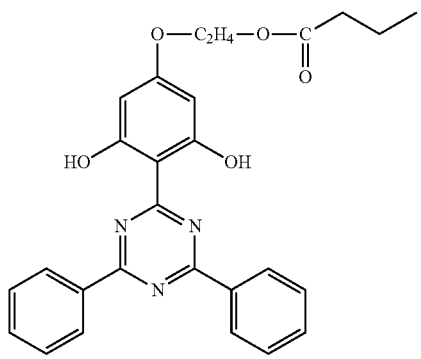
[Chem. 12]
Compound No. 8
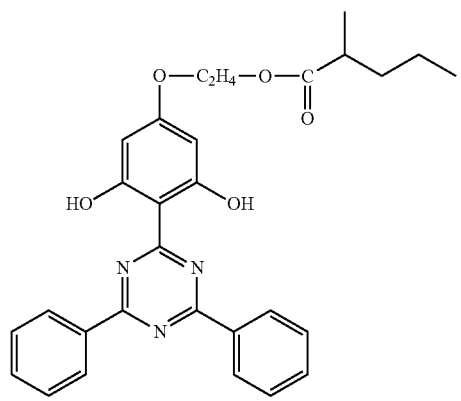

-continued
Compound No. 9
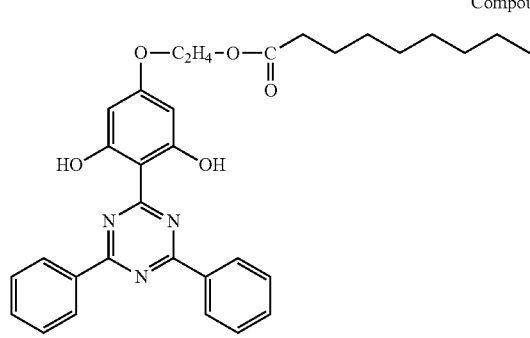
Compound No. 10
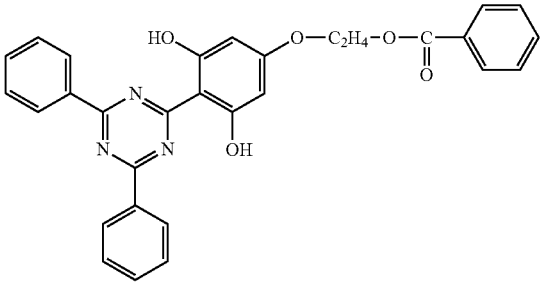
Compound No. 11
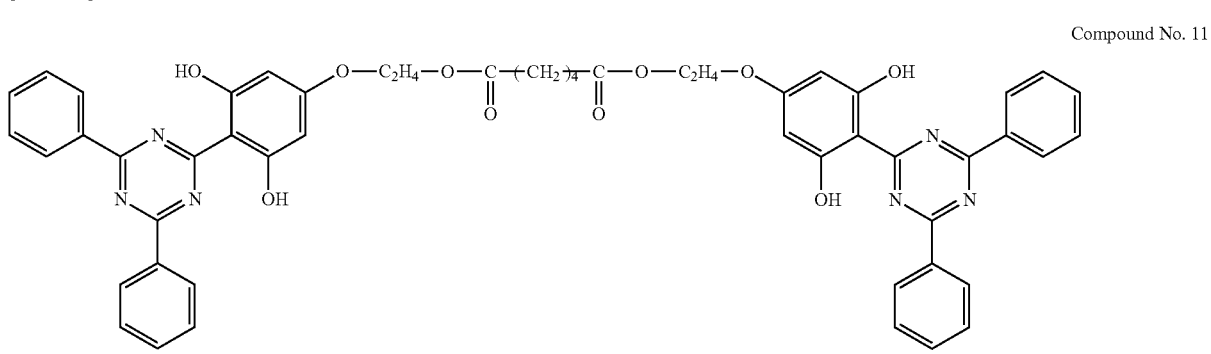
Compound No. 12
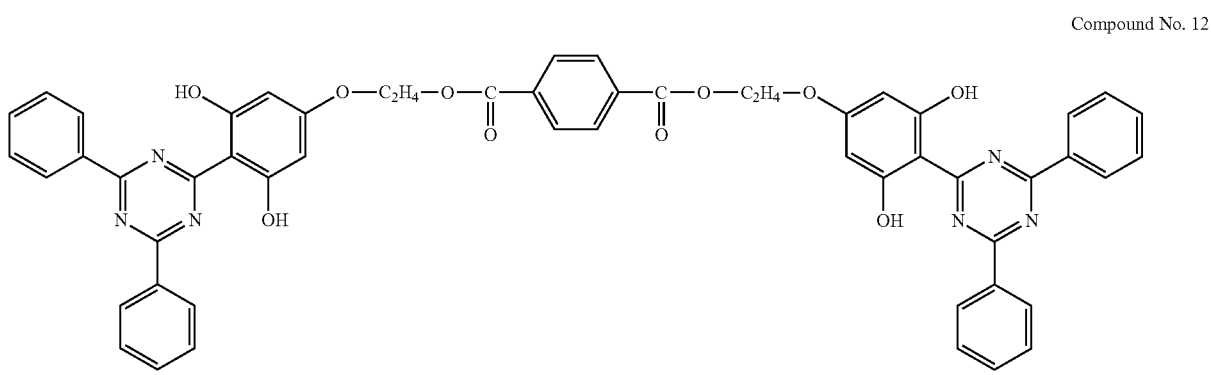
Compound No. 13
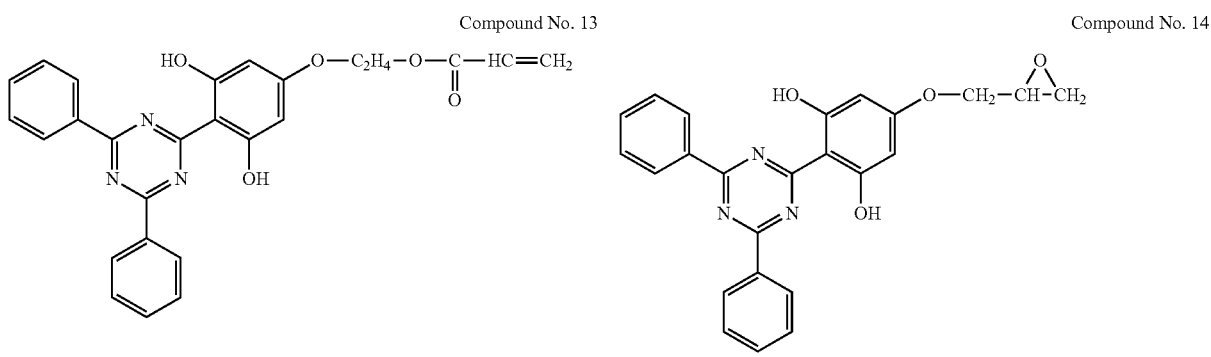
Compound No. 14
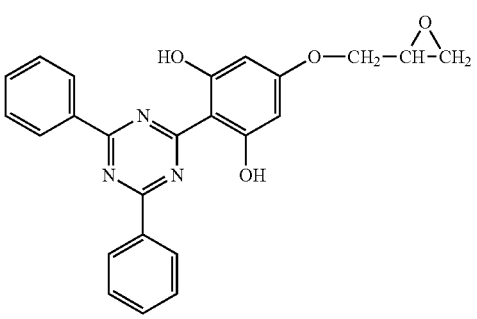

[Chem. 19]

Compound No. 15

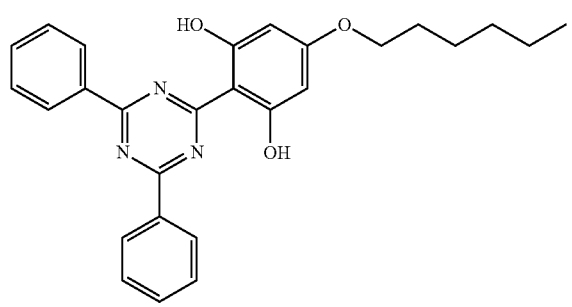

[Chem. 20]

Compound No. 16

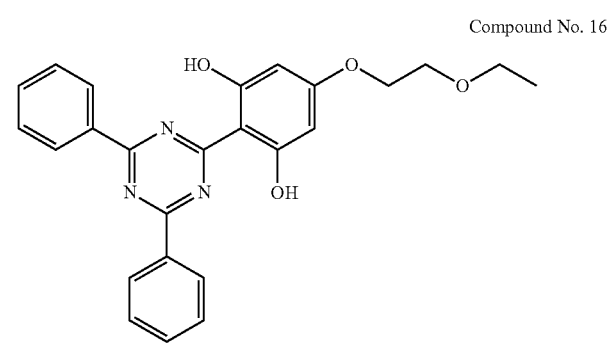

[Chem. 21]

Compound No. 17

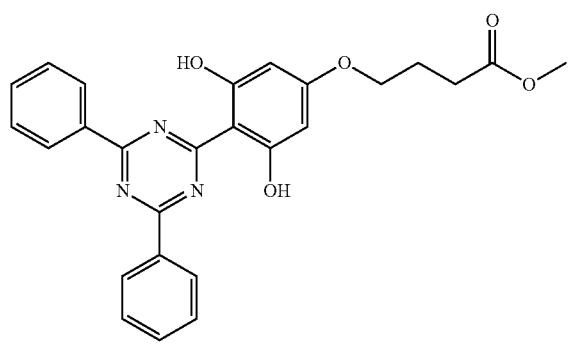

[Chem. 22]

Compound No. 18

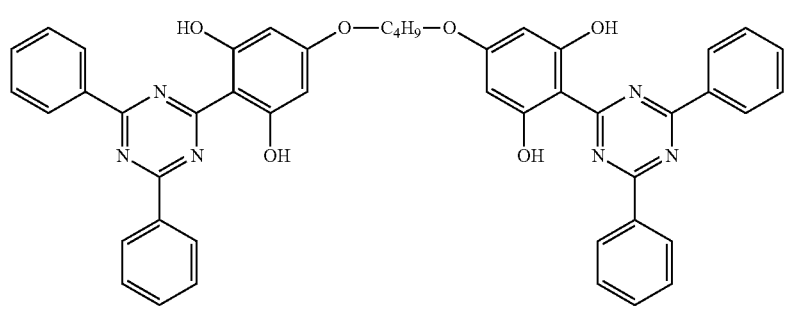

[Chem. 23]

Compound No. 19

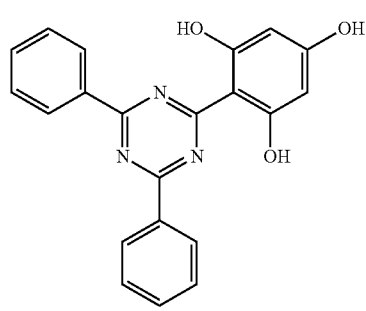

[Chem. 24]

Compound No. 20

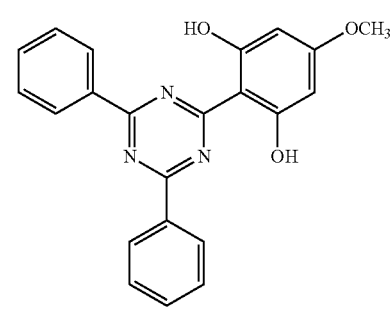

Next, a synthetic resin composition of the present invention will be described.

The synthetic resin composition of the present invention contains the above-described ultraviolet absorbing agent.

The blending amount of the ultraviolet absorbing agent is preferably 0.001 parts by mass to 20 parts by mass, more preferably 0.01 to 10 parts by mass, and even more preferably 0.1 to 5 parts by mass with respect to 100 parts by mass of a synthetic resin. If the blending amount of the ultraviolet absorbing agent is less than 0.001 parts by mass, sufficient effects cannot be obtained, and if the blending amount exceeds 20 parts by mass, there is a possibility that the effect of adding the ultraviolet absorbing agent will not be improved, and the physical properties of a resin will be influenced.

Specific examples of the synthetic resin used in the synthetic resin composition of the present invention include α-olefin polymers such as polypropylene, high-density polyethylene, low-density polyethylene, linear low-density polyethylene, cross-linked polyethylene, ultra high molecular weight polyethylene, polybutene-1, and poly-3-methylpentene, or polyolefins and copolymers thereof such as ethylene vinyl-acetate copolymers, ethylene-ethylacrylate copolymers, and ethylene-propylene copolymers; halogen-containing resins such as polyvinyl chloride, polyvinylidene chloride, chlorinated polyethylene, chlorinated polypropylene, polyvinylidene fluoride, chlorinated rubber, vinyl chloride-vinyl acetate copolymers, vinyl chloride-ethylene copolymers, vinyl chloride-vinylidene chloride copolymers, vinyl chloride-vinylidene chloride-vinyl acetate terpolymers, vinyl chloride-acrylic ester copolymers, vinyl chloride-maleic acid ester copolymers, vinyl chloride-cyclohexyl maleimide copolymers; petroleum resins, coumarone resins, polystyrene, polyvinyl acetate, acrylic resins, polymethyl methacrylate, polyvinyl alcohols, polyvinyl formal, and polyvinyl butyral; aromatic polyesters such as polyalkylene terephthalates (e.g., polyethylene terephthalate, polybutylene terephthalate, and polycyclohexanedimethylene terephthalate) and polyalkylene naphthalates (e.g., polyethylene naphthalate and polybutylene naphthalate), and linear polyesters such as polytetramethylene terephthalate; degradable aliphatic polyesters such as polyhydroxybutyrate, polycaprolactone, polybutylene succinate, polyethylene succinate, polylactic resins, polymalic acid, polyglycolic acid, polydioxanes, and poly (2-oxetanone); polyamides (e.g., polyphenylene oxide, polycaprolactam, and polyhexamethylene adipamide), thermoplastic resins (e.g., polycarbonates, branched polycarbonates, polyacetal, polyphenylene sulfide, polyurethane, and cellulose-based resins), and products obtained by blending thereof, or thermosetting resins such as phenol resins, urea resins, melamine resins, epoxy resins, and unsaturated polyester resins, fluorine resins, silicone resins, silicone rubber polyethersulfone, polysulfone, polyphenylene ethers, polyether ketones, polyether ether ketones, and liquid crystal polymers. Furthermore, the examples include isoprene rubber, butadiene rubber, acrylonitrile-butadiene copolymer rubber, styrene-butadiene copolymer rubber, fluororubber, and silicone rubber.

Moreover, specific examples of the synthetic resin include olefin-based thermoplastic elastomers, styrene-based thermoplastic elastomers, polyester-based thermoplastic elastomers, nitrile-based thermoplastic elastomers, nylon-based thermoplastic elastomers, vinyl chloride-based thermoplastic elastomers, polyamide-based thermoplastic elastomers, and polyurethane-based thermoplastic elastomers. These synthetic resins may be used alone or in combination of two or more. Also, the synthetic resin may be alloyed.

The above-described synthetic resins used in the present invention can be used regardless of a molecular weight, the degree of polymerization, a density, a softening point, a ratio of insoluble portions to a solvent, the degree of stereoregularity, whether a catalytic residue remains, the type and blending ratio of monomer that serves as a raw material, the type of polymerization catalysts (for example, Ziegler catalyst, metallocene catalysts), and the like.

Various additive agents such as phenol-based antioxidants, phosphorus-based antioxidants, thioether-based antioxidants, ultraviolet absorbing agents other than the ultraviolet absorbing agent of the present invention, and hindered amine-based photostabilizers can be further added as needed to the synthetic resin composition of the present invention, and addition of these additive agents can stabilize the resin composition of the present invention.

Examples of the above-described phenol-based antioxidants include 2,6-di-tert-butyl-p-cresol, 2,6-diphenyl-4-octadecyloxyphenol, distearyl (3,5-di-tert-butyl-4-hydroxybenzyl) phosphonate, 1,6-hexamethylenebis[(3,5-di-tert-butyl-4-hydroxyphenyl) propionamide], 4,4'-thiobis (6-tert-butyl-m-cresol), 2,2'-methylenebis(4-methyl-6-tert-butylphenol), 2,2'-methylenebis(4-ethyl-6-tert-butylphenol), 4,4'-butylidenebis(6-tert-butyl-m-cresol), 2,2'-ethylidenebis(4,6-di-tert-butylphenol), 2,2'-ethylidenebis(4-sec-butyl-6-tert-butylphenol), 1,1,3-tris (2-methyl-4-hydroxy-5-tert-butylphenyl) butane, 1,3,5-tris(2,6-dimethyl-3-hydroxy-4-tert-butylbenzyl) isocyanurate, 1,3,5-tris (3,5-di tert-butyl-4-hydroxybenzyl) isocyanurate, 1,3,5-tris (3,5-di-tert-butyl-4-hydroxybenzyl)-2,4,6-trimethylbenzene, 2-tert-butyl-4-methyl-6-(2-acryloyloxy-3-tert-butyl-5-methylbenzyl) phenol, stearyl(3,5-di-tert-butyl-4-hydroxyphenyl) propionate, tetrakis[3-(3,5-di-tert-butyl-4-hydroxyphenyl) methyl propionate] methane, thiodiethylene glycol bis[(3,5-di-tert-butyl-4-hydroxyphenyl) propionate], 1,6-hexamethylene bis[(3,5-di-tert-butyl-4-hydroxyphenyl) propionate], bis[3,3-bis(4-hydroxy-3-tert-butylphenyl) butyric acid] glycol esters, bis[2-tert-butyl-4-methyl-6-(2-hydroxy-3-tert-butyl-5-methylbenzyl) phenyl] terephthalate, 1,3,5-tris[(3,5-di-tert-butyl-4-hydroxyphenyl) propionyl oxyethyl] isocyanurate, 3,9-bis[1,1-dimethyl-2-{(3-tert-butyl-4-hydroxy-5-methylphenyl) propionyloxy} ethyl]-2,4,8,10-tetraoxaspiro[5,5]undecane, and triethylene glycol bis[(3-tert-butyl-4-hydroxy-5-methylphenyl) propionate]. An addition amount of these phenol-based antioxidants is preferably 0.001 to 10 parts by mass, and more preferably 0.05 to 5 parts by mass with respect to 100 parts by mass of a synthetic resin.

Examples of the above-described phosphorus-based antioxidants include tris(nonylphenyl) phosphite, tris[2-tert-butyl-4-(3-tert-butyl-4-hydroxy-5-methylphenylthio)-5-methylphenyl] phosphite, tridecyl phosphite, octyl diphenyl phosphite, di(decyl) monophenyl phosphite, di(tridecyl)pentaerythritol diphosphite, di(nonylphenyl) pentaerythritol diphosphite, bis(2,4-di-tert-butylphenyl) pentaerythritol diphosphite, bis(2,6-di-tert-butyl-4-methylphenyl) pentaerythritol diphosphite, bis(2,4,6-tri-tert-butylphenyl) pentaerythritol diphosphite, bis(2,4-dicumyl phenyl) pentaerythritol diphosphite, tetra(tridecyl) isopropylidenediphenol diphosphite, tetra(tridecyl)-4,4'-n-butylidene bis(2-tert-butyl-5-methylphenol diphosphite, hexa(tridecyl)-1,1,3-tris(2-methyl-4-hydroxy-5-tert-butylphenyl) butane triphosphite, tetrakis(2,4-di-tert-butylphenyl) biphenylene diphosphonite, 9,10-dihydro-9-oxa-10-phosphaphenanthrene-10-oxide, 2,2'-methylene bis(4,6-tert-butyl-phenyl)-2-ethylhexyl phosphite, 2,2'-methylenebis(4,6-tert-butylphenyl)-octadecyl phosphite, 2,2'-ethylidene-bis (4,6-di-tert-butylphenyl)fluorophosphite, tris(2-[(2,4,8,10-tetrakis-tert-butyl dibenzo[d, f][1,3,2]dioxaphosphepin-6-yl) oxy] ethyl) amine, and phosphites of 2-ethyl-2-butyl propylene glycol, and 2,4,6-tri-tert-butylphenol. An addition amount of these phosphorus-based antioxidants is preferably 0.001 to 10 parts by mass, and more preferably 0.05 to 5 parts by mass with respect to 100 parts by mass of a synthetic resin.

Examples of the thioether-based antioxidants include dialkyl thiodipropionates such as dilauryl thiodipropionate, dimyristyl thiodipropionate, and distearyl thiodipropionate, and pentaerythritol tetra (β-alkyl thiopropionate) esters. An addition amount of these thioether-based antioxidants is preferably 0.001 to 10 parts by mass, and more preferably 0.05 to 5 parts by mass with respect to 100 parts by mass of a synthetic resin.

Examples of ultraviolet absorbing agents other than the ultraviolet absorbing agent of the present invention above include 2-hydroxybenzophenones such as 2,4-dihydroxybenzophenone, 2-hydroxy-4-methoxybenzophenone, 2-hydroxy-4-octoxybenzophenone, and 5,5'-methylenebis(2-hydroxy-4-methoxybenzophenone); 2-(T-hydroxyphenyl) benzotriazoles such as 2-(2'-hydroxy-5'-methylphenyl) benzotriazole, 2-(2'-hydroxy-3',5'-di-ten-butylphenyl)-5-chlorobenzotriazole, 2-(2'-hydroxy-3'-tert-butyl-5'-methylphenyl)-5-chlorobenzotriazole, 2-(2'-hydroxy-5'-tert-octylphenyl) benzotriazole, 2-(2'-hydroxy-3',5'-dicumyl phenyl) benzotriazole, 2,2'-methylenebis(4-tert-octyl-6-(benzotriazolyl) phenol), and 2-(2-hydroxy-3'-tert-butyl-5'-carboxyphenyl) benzotriazole; benzoates such as phenyl salicylate, resorcinol monobenzoate, 2,4-di-tert-butyl-phenyl-3,5-di-tert-butyl-4-hydroxybenzoate, 2,4-di-tert-amyl-phenyl-3,5-di-tert-butyl-4-hydroxybenzoate, hexadecyl-3,5-di-tert-butyl-4-hydroxy benzoate; substituted oxanilides such as 2-ethyl-2'-ethoxy oxanilide and 2-ethoxy-4'-dodecyl oxanilide; cyanoacrylates such as ethyl-α-cyano-β,β-diphenyl acrylate, and methyl-2-cyano-3-methyl-3-(p-methoxyphenyl) acrylate; triaryl triazines such as 2-(2-hydroxy-4-octoxyphenyl)-4,6-bis(2,4-di-tert-butylphenyl)-s-triazine, 2-(2-hydroxy-4-methoxyphenyl)-4,6-diphenyl-s-triazine, and 2-(2-hydroxy-4-propoxy-5-methylphenyl)-4,6-bis(2,4-di-tert-butylphenyl)-s-triazine. An addition amount of these ultraviolet absorbing agents other than the ultraviolet absorbing agent of the present invention is preferably 0.001 to 30 parts by mass, and more preferably 0.05 to 10 parts by mass with respect to 100 parts by mass of a synthetic resin.

Examples of the above-described hindered amine-based photostabilizers include hindered amine compounds such as 2,2,6,6-tetramethyl-4-piperidyl stearate, 1,2,2,6,6-pentamethyl-4-piperidyl stearate, 2,2,6,6-tetramethyl-4-piperidyl benzoate, bis(2,2,6,6-tetramethyl-4-piperidyl) sebacate, bis(1,2,2,6,6-tetramethyl-4-piperidyl) sebacate, bis(1-octoxy-2,2,6,6-tetramethyl-4-piperidyl) sebacate, tetrakis(2,2,6,6-tetramethyl-4-piperidyl)-1,2,3,4-butane tetracarboxylate, tetrakis(1,2,2,6,6-pentamethyl-4-piperidyl)-1,2,3,4-butane tetracarboxylate, bis(2,2,6,6-tetramethyl-4-piperidyl)di(tridecyl)-1,2,3,4-butane tetracarboxylate, bis(1,2,2,6,6-pentamethyl-4-piperidyl)di(tridecyl)-1,2,3,4-butane tetracarboxylate, bis(1,2,2,4,4-pentamethyl-4-piperidyl)-2-butyl-2-(3,5-di-tert-butyl-4-hydroxybenzyl) malonate, 1-(2-hydroxyethyl)-2,2,6,6-tetramethyl-4-piperidinol/diethyl succinate polycondensate, 1,6-bis(2,2,6,6-tetramethyl-4-piperidyl amino) hexane/2,4-dichloro-6-morpholino-s-triazine polycondensates, 1,6-bis(2,2,6,6-tetramethyl-4-piperidylamino) hexane/2,4-dichloro-6-tert-octyl-amino-s-triazine polycondensates, 1,5,8,12-tetrakis[2,4-bis(N-butyl-N-(2,2,6,6-tetramethyl-4-piperidyl) amino)-s-triazin-6-yl]-1,5,8,12-tetra-azadodecane, 1,5,8,12-tetrakis[2,4-bis(N-butyl-N-(1,2,2,6,6-pentamethyl-4-piperidyl) amino)-s-triazin-6-yl]-1,5,8-12-tetra-azadodecane, 1,6,11-tris[2,4-bis(N-butyl-N-(2,2,6,6-tetramethyl-4-piperidyl) amino)-s-triazin-6-yl] aminoundecane, and 1,6,11-tris[2,4-bis(N-butyl-N-(1,2,2,6,6-pentamethyl-4-piperidyl) amino)-s-triazin-6-yl] aminoundecane. An addition amount of these hindered amine-based photostabilizers is preferably 0.001 to 30 parts by mass, and more preferably 0.05 to 10 parts by mass with respect to 100 parts by mass of a synthetic resin.

Also, if a polyolefin-based resin is used as the synthetic resin, it is preferable to add a known neutralizer as needed in order to neutralize a residual catalyst in the polyolefin resin. Examples of the neutralizer include fatty acid metal salts such as calcium stearate, lithium stearate, and sodium stearate, and fatty acid amide compounds such as ethylene-bis-(stearamide), ethylene-bis(12-hydroxystearamide), and stearic acid amides, and these neutralizers may be mixed.

Nucleating agents such as aromatic carboxylic acid metal salts, alicyclic alkyl carboxylic acid metal salts, aluminum p-tert-butylbenzoate, metal salts of aromatic phosphoric acid esters, and dibenzylidene sorbitols, metal soaps, hydrotalcites, triazine ring-containing compounds, metal hydroxides, phosphoric acid ester-based flame retardants, condensed phosphoric acid ester-based flame retardants, phosphate-based flame retardants, inorganic phosphorus-based flame retardants, (poly) phosphate-based flame retardants, halogen-based flame retardants, silicone-based flame retardants, antimony oxides such as antimony trioxide, other inorganic flame-retardant auxiliaries, other organic flame-retardant auxiliaries, fillers, pigments, lubricants, foaming agents, and charge inhibitors may be further added as needed to the synthetic resin composition of the present invention.

Examples of the above-described triazine ring-containing compound include melamine, ammeline, benzoguanamine, acetoguanamine, phthalodiguanamine, melaminecyanurate, melamine pyrophosphate, butylene diguanamine, norbornene diguanamine, methylene diguanamine, ethylene dimelamine, trimethylene dimelamine, tetramethylene dimelamine, hexamethylene dimelamine, and 1,3-hexylene dimelamine.

Examples of the above-described metal hydroxide include magnesium hydroxide, aluminum hydroxide, calcium hydroxide, barium hydroxide, zinc hydroxide, and KISUMA 5A (magnesium hydroxide: produced by Kyowa Chemical Industry Co., Ltd.).

Examples of the phosphoric acid ester-based flame retardant include trimethyl phosphate, triethyl phosphate, tributyl phosphate, tributoxyethyl phosphate, tris(chloroethyl) phosphate, tris(dichloropropyl) phosphate, triphenyl phosphate, tricresyl phosphate, cresyl diphenyl phosphate, trixylenyl phosphate, octyl diphenyl phosphate, xylenyl diphenyl phosphate, tris(isopropylphenyl) phosphate, 2-ethylhexyl diphenyl phosphate, t-butylphenyl diphenyl phosphate, bis-(t-butylphenyl) phenyl phosphate, tris-(t-butylphenyl) phosphate, isopropylphenyl diphenyl phosphate, bis-(isopropylphenyl) diphenyl phosphate, and tris-(isopropylphenyl) phosphate.

Examples of the above-described condensed phosphoric acid ester-based flame retardant include 1,3-phenylene bis (diphenyl phosphate), 1,3-phenylene bis(dixylenyl phosphate), and bisphenol A bis(diphenyl phosphate).

Examples of the above-described (poly)phosphate-based flame retardant include ammonium salts and amine salts of (poly)phosphoric acid such as ammonium polyphosphate, melamine polyphosphate, piperazine polyphosphate, melamine pyrophosphate, and piperazine pyrophosphate.

Examples of the other inorganic flame-retardant auxilary include inorganic compounds such as titanium oxide, aluminum oxide, magnesium oxide, hydrotalcite, talc, and montmorillonite, and products obtained by performing surface treatment on these compounds, and various commercially-available products such as TIPAQUE R-680 (titanium oxide: produced by ISHIHARA SANGYO KAISHA, Kyowamag 150 (magnesium oxide: produced by Kyowa Chemical Industry Co., Ltd.), DHT-4A (hydrotalcite: produced by Kyowa Chemical Industry Co., Ltd.), and alcamizer 4 (zinc-modified hydrotalcite: produced by Kyowa Chemical Industry Co., Ltd.) can be used. Also, an example of the other organic flame-retardant auxilary is pentaerythritol.

In addition, an additive agent that is usually used in a synthetic resin as needed, for example, cross-linking agents, anti-clouding agents, plate-out preventing agents, surface treatment agents, plasticizers, lubricants, flame retardants, fluorescent agents, antifungal agents, bactericides, foaming agents, metal deactivators, release agents, pigments, processing aids, antioxidants, and photostabilizers may be blended into the synthetic resin composition of the present invention, in such a range that the effect of the present invention is not impaired.

A molded article can be obtained by molding the synthetic resin composition of the present invention. There is no particular limitation on the molding method, and examples thereof include extrusion, calendering, injection molding, rolling, compression molding, blow molding, and rotational molding. Molded products having various shapes, such as resin plates, sheet, films, bottles, fibers, and profiles can be manufactured. Also, films and sheets can be manufactured with a cast film method.

The synthetic resin composition of the present invention and a molded article made of this synthetic resin composition can be used in broad industrial fields such as electrical, electronic, and communication, agriculture, forestry and fisheries, mining, construction, food, textile, clothing, medical care, coal, petroleum, rubber, leather, automobiles, precision equipment, wood, building materials, civil engineering, furniture, printing, and musical instruments.

More specifically, the synthetic resin composition of the present invention and the molded article thereof are used for applications in business equipment and OA equipment such as printers, personal computers, word processors, keyboards, PDAs (small information terminals), phones, copiers, facsimiles, ECRs (electronic cash registers), calculators, electronic notebooks, cards, holders, and office stationeries, home appliances such as washing machines, refrigerators, vacuum cleaners, microwave ovens, lighting equipment, game machines, irons, and foot warmers, AV equipment such as TVs, VTRs, video cameras, radio cassette recorders, tape recorders, mini-discs, CD players, speakers, and liquid crystal displays, electrical and electronic components, and communication equipment such as connectors, relays, condensers, switches, printed circuit boards, coil bobbins, semiconductor sealing materials, LED sealing materials, electric wires, cables, transformers, deflection yokes, distribution boards, and watches, exterior materials for automobiles, prepress films, adhesive films, bottles, food containers, films for food packaging, pharmaceutical and pharmaceutical wrap films, product packaging films, agricultural films, agricultural sheet, and greenhouse films.

Moreover, the synthetic resin composition of the present invention and the molded article thereof can be used for various applications in cars, vehicles, ships, aircrafts, buildings, residential, construction materials, and civil engineering materials for seats (paddings, outer materials, etc.), belts, ceilings, compatible tops, armrests, door trims, rear package trays, carpets, mats, sun visors, wheel covers, mattress covers, air bags, heat insulating materials, hand straps, hand strap bands, wire coating materials, electrical insulating materials, paints, coating materials, overlay materials, floorings, corner walls, carpets, wallpapers, wall coverings, exterior materials, interior materials, roofing, deck materials, wall materials, studs, floor plates, fence materials, skeleton and moldings, and windows and door profiles, shingles, sidings, terraces, balconies, sound insulation boards, heat insulating boards, and window materials, life supplies, and sporting goods such as clothing, curtains, sheets, non-woven fabric, plywood, synthetic fiber boards, carpets, entrance mats, sheets, buckets, hoses, containers, glasses, bags, cases, goggles, skis, rackets, tents, and musical instruments.

The ultraviolet absorbing agent of the present invention can be used not only in the synthetic resin composition and a molded article thereof, films, and fibers, but also in paints, cosmetics, and the like.

EXAMPLES

Hereinafter, the present invention will be described in detail by way of Examples. However, the present invention is not limited to the following Examples.

Example 1

15 g of 2-(4,6-diphenyl-1,3,5-triazin-2-yl)-1,3,5-trihydroxybenzene, 6.8 g of ethylene carbonate, 1 g of sodium carbonate, and 50 mL of dimethylacetoamide were added to a 200-ml four-neck flask, and were reacted at 140° C. for 7 hours. After the reaction ended and then the flask was cooled down to the room temperature, 2-(4,6-diphenyl-1,3,5-triazin-2-yl)-5-(2-hydroxyethoxy)-1,3-dihydroxybenzene was obtained by filtering.

Next, 15 g of 2-(4,6-diphenyl-1,3,5-triazin-2-yl)-5-(2-hydroxyethoxy)-1,3-dihydroxybenzene, 5.7 g of 2-ethyl hexoic acid, 1.36 g of p-toluenesulfonic acid, and 43 g of xylene were added to a 200-ml four-neck flask, and were reacted for 9 hours in a reflux state. When isopropanol was added after the reaction ended, yellow powder was deposited. This mixture was filtered and dried to obtain Compound No. 1 below, which is an ultraviolet absorbing agent of the present invention.

The structure of Compound No. 1 above was identified using the following peaks through performing NMR measurement using an NMR (ASCEND 500 produced by BRUKER).

$^1$H NMR (CDCl$_3$, δ in ppm) 13.677 (m, 1H, Ph-OH), 11.097 (d, 4H, Ar), 7.665-7.285 (m, 6H, Ar), 7.258 (s, 1H, Ph-OH), 6.121 (s, 2H, Ar), 4.462 (d, 2H, —CH2-), 4.422 (d, 2H, —CH2-), 2.341 (s, 1H, COCH—), 1.546-1.200 (m 8H, CH2), 0.915 (t, 6H, CH3).

Also, the maximum absorption wavelength of Compound No. 1 was measured with a spectrophotometer (V670 produced by JASCO Corporation). The maximum absorption wavelengths were 279 nm and 323 nm, and molar extinction coefficients at the respective wavelengths were $3.65 \times 10^4$ and $2.18 \times 10^4$.

[Chem. 25]

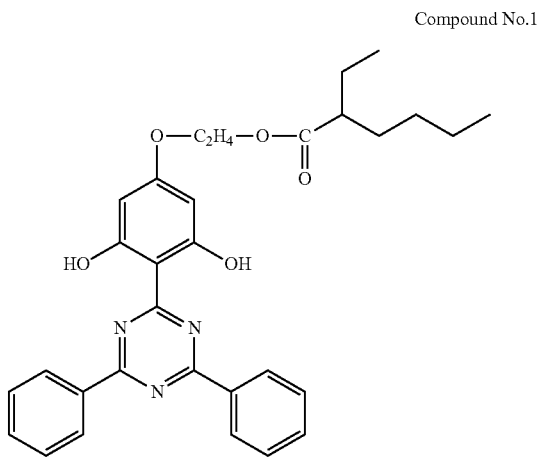

Compound No.1

Comparative Example 1

The maximum absorption wavelength of Comparative Compound-1 below, which is a conventional known triazine-based ultraviolet absorbing agent, was measured with a spectrophotometer (V670 produced by JASCO Corporation). The maximum absorption wavelengths were 278 nm and 340 nm, and molar extinction coefficients at the respective wavelengths were $3.04 \times 10^4$ and $1.41 \times 10^4$.

[Chem. 26]

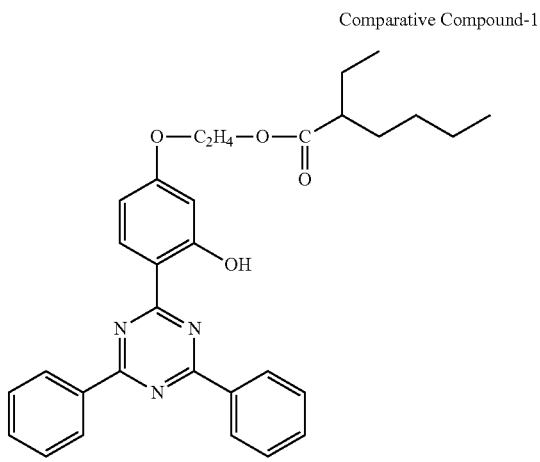

Comparative Compound-1

It can be said from the results obtained in Example 1 and Comparative Example 1 that Compound No. 1, which is the ultraviolet absorbing agent of the present invention, has a stronger absorbability in the UV-A region than the triazine-based ultraviolet absorbing agent of Comparative Compound-1, and is a useful ultraviolet absorbing agent.

Example 2

33.8 mg of Compound No. 1 that was obtained in Example 1 and 1.125 g of polymethyl methacrylate were introduced into a 25-ml volumetric flask, and dichloromethane was added to a marked line. After the volumetric flask was left at room temperature for 1 hour so that Compound No. 1 was dissolved, this solution was introduced into a Petri dish (diameter: 60 mm) with a 4-mL transfer pipette, and was dried at room temperature for 30 minutes. After the solution was dried, a film was peeled off from the Petri dish to obtain polymethyl methacrylate film having a thickness of 50 μm.

The obtained polymethyl methacrylate film was subjected to a weatherability test with a METAL WEATHER (produced by DAIPLA WINTES, CO., LTD.) under ultraviolet irradiation conditions where a temperature was 63° C., a humidity of 50% RH, 295-780 nm, and 75 mW/cm$^2$, and color differences (ΔE) in an L*a*b*color system after 100-hour irradiation, 200-hour irradiation, and 300-hour irradiation were measured using a spectrophotometer SC-T that is produced by Suga Test Instruments Co., Ltd. Results are shown in Table 1.

Comparative Example 2

A polymethyl methacrylate film was produced in the same manner as in Example 2 except that Comparative Compound-1 above was used instead of Compound No. 1, and the weatherability test was performed in the same manner as in Example 2. Results are shown in Table 1.

TABLE 1

|  | ΔE 100 hours | ΔE 200 hours | ΔE 300 hours |
| --- | --- | --- | --- |
| Example 2 Compound No. 1 | 6.8 | 11.7 | 13.5 |
| Comparative Example 2 Comparative Compound-1 | 9.2 | 17.9 | 18.4 |

From the results of color differences (ΔE) that were obtained in Example 2 and Comparative Example 2, it can be understood that the polymethyl methacrylate film that was produced using Compound No. 1 of the present invention was unlikely to turn color even in the case of being subjected to ultraviolet irradiation, compared to the polymethyl methacrylate film that was produced using Comparative Compound-1, and has excellent weatherability. Accordingly, it was found that the ultraviolet absorbing agent of the present invention can provide a synthetic resin with excellent weatherability.

INDUSTRIAL APPLICABILITY

According to the present invention, it is possible to provide an ultraviolet absorbing agent that efficiently absorbs ultraviolet rays in a wide wavelength region, and in particular, has a strong absorbability even in the UV-A region. Also, according to the present invention, it is possible to provide a synthetic resin composition with excellent weatherability.

The invention claimed is:
1. An ultraviolet absorbing agent comprising a triazine-based compound represented by Formula (1),

[Chem. 1]

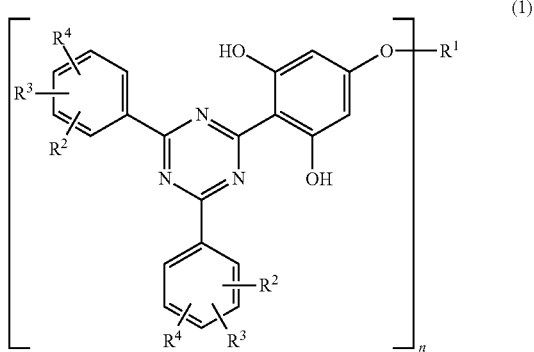

wherein n indicates 1 or 2,
when n is 1, $R^1$ represents a hydrogen atom, an alkyl group having 1 to 20 carbon atoms, a cycloalkyl group having 3 to 8 carbon atoms, an alkenyl group having 3 to 8 carbon atoms, an aryl group having 6 to 18 carbon atoms, an alkylaryl group having 7 to 19 carbon atoms, an arylalkyl group having 7 to 19 carbon atoms, or a glycidyl group,
when n is 2, $R^1$ represents an alkylene group having 1 to 20 carbon atoms, a cycloalkylene group having 3 to 8 carbon atoms, an arylene group having 6 to 18 carbon atoms, or a combination thereof,
each group represented by $R^1$ is optionally substituted with an alkyl group having 1 to 8 carbon atoms, an alkoxy group having 1 to 8 carbon atoms, an aryl group having 6 to 12 carbon atoms, an alkylaryl group having 7 to 13 carbon atoms, an arylalkyl group having 7 to 13 carbon atoms, a hydroxy group, a halogen atom, or a glycidyl group, or is optionally interrupted with an oxygen atom, a sulfur atom, a carbonyl group, an ester group, an amide group, or an imido group, or these substitution and interruption are optionally combined, and
$R^2$, $R^3$, and $R^4$ may be identical to or different from each other, and each represent a hydrogen atom, a halogen atom, an alkyl group having 1 to 4 carbon atoms, or an alkoxy group having 1 to 4 carbon atoms.
2. The ultraviolet absorbing agent of claim 1, wherein each group represented by $R^1$ is substituted with an alkyl group having 1 to 8 carbon atoms, an alkoxy group having 1 to 8 carbon atoms, an aryl group having 6 to 12 carbon atoms, an alkylaryl group having 7 to 13 carbon atoms, an arylalkyl group having 7 to 13 carbon atoms, a hydroxy group, a halogen atom, or a glycidyl group.
3. The ultraviolet absorbing agent of claim 1, wherein each group represented by $R^1$ is interrupted with an oxygen atom, a sulfur atom, a carbonyl group, an ester group, an amide group, or an imido group.
4. The ultraviolet absorbing agent of claim 1, wherein each group represented by $R^1$ represents a combination of substitutions and interruptions,
wherein the substitutions are with an alkyl group having 1 to 8 carbon atoms, an alkoxy group having 1 to 8 carbon atoms, an aryl group having 6 to 12 carbon atoms, an alkylaryl group having 7 to 13 carbon atoms, an arylalkyl group having 7 to 13 carbon atoms, a hydroxy group, a halogen atom, or a glycidyl group, and
wherein the interruptions are with an oxygen atom, a sulfur atom, a carbonyl group, an ester group, an amide group, or an imido group.
5. The ultraviolet absorbing agent according to claim 1, wherein the triazine-based compound represented by Formula (1) is a triazine-based compound represented by Formula (2),

[Chem. 2]

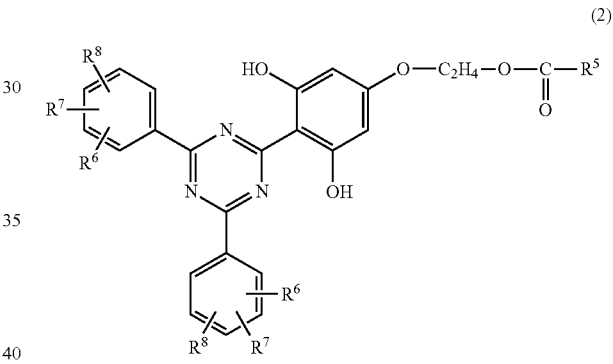

wherein, $R^5$ represents a linear or branched alkyl group having 1 to 12 carbon atoms, and
$R^6$, $R^7$, and $R^8$ may be identical to or different from each other, and each represent a hydrogen atom or a linear or branched alkyl group having 1 to 4 carbon atoms.
6. A synthetic resin composition comprising a synthetic resin and the ultraviolet absorbing agent according to claim 1.
7. A synthetic resin composition comprising a synthetic resin and the ultraviolet absorbing agent according to claim 5.

* * * * *